United States Patent
Bruhns

(10) Patent No.: US 12,370,703 B2
(45) Date of Patent: Jul. 29, 2025

(54) REPLACEABLE BLADE KNIFE

(71) Applicant: Hogue Tool & Machine, Inc., Paso Robles, CA (US)

(72) Inventor: James David Bruhns, Templeton, CA (US)

(73) Assignee: HOGUE TOOL & MACHINE, INC., Paso Robles, CA (US)

( * ) Notice: Subject to any disclaimer, the term of this patent is extended or adjusted under 35 U.S.C. 154(b) by 210 days.

(21) Appl. No.: 17/961,242

(22) Filed: Oct. 6, 2022

(65) Prior Publication Data
US 2023/0173696 A1    Jun. 8, 2023

Related U.S. Application Data

(60) Provisional application No. 63/287,107, filed on Dec. 8, 2021.

(51) Int. Cl.
B26B 5/00    (2006.01)

(52) U.S. Cl.
CPC ...................... B26B 5/00 (2013.01)

(58) Field of Classification Search
CPC ........................................ B26B 5/00
USPC ........................................... 30/339
See application file for complete search history.

(56) References Cited

U.S. PATENT DOCUMENTS

| | | | | |
|---|---|---|---|---|
| 3,244,317 A * | 4/1966 | Raybin | ............... | A61B 17/3215 206/370 |
| 3,262,205 A * | 7/1966 | Arden | ............... | A61B 17/3213 D24/147 |
| 4,922,614 A * | 5/1990 | Machida | ............... | B26B 5/00 606/167 |
| 5,312,429 A | 5/1994 | Noack | | |
| 8,181,352 B1 * | 5/2012 | Shackelford, Sr. | ............... | A61B 17/3217 30/162 |
| 8,898,910 B2 * | 12/2014 | Ichiyanagi | ............... | B25G 1/04 30/162 |
| 11,090,820 B1 * | 8/2021 | Wu | ............... | A61B 17/3213 |

(Continued)

OTHER PUBLICATIONS

Havalonknives, "How do you change a Havalon Blade?" https://www.youtube.com/watch?v=mUm6gHqXea0, Published Oct. 19, 2015, Accessed May 25, 2022.

(Continued)

Primary Examiner — Omar Flores Sanchez
(74) Attorney, Agent, or Firm — Bennet K. Langlotz; Langlotz Patent & Trademark Works, LLC

(57) ABSTRACT

Replaceable blade knives have an elongated body having opposed ends, a handle portion extending to a handle end of the elongated body, and a blade attachment facility at an opposed forward end of the elongated body, the blade attachment facility having a blade support surface configured to abut a major face portion of the planar blade proximate the elongated aperture, an elongated boss sized to closely receive the elongated aperture of the planar blade, the elongated boss defining an undercut configured to receive a blade portion at the constriction to prevent separation of the planar blade from the blade support surface when the planar blade is in an installed condition with the elongated boss received in the elongated aperture, and a movable ejector element connected to the elongated body and operable to engage the rear end of the planar blade to eject the planar blade from the holder.

17 Claims, 14 Drawing Sheets

(56) References Cited

U.S. PATENT DOCUMENTS

| | | | |
|---|---|---|---|
| 11,278,310 B2 | 3/2022 | Austria et al. | |
| 2014/0142600 A1* | 5/2014 | Kumar | A61B 17/3213 |
| | | | 606/167 |
| 2016/0249947 A1* | 9/2016 | Castanon | A61B 17/3213 |
| | | | 606/167 |
| 2017/0151682 A1* | 6/2017 | Cheng | B26B 5/00 |
| 2017/0265882 A1* | 9/2017 | Austria | A61B 17/3211 |

OTHER PUBLICATIONS

International Search Report for PCT/US22/52151.
Written Opinion of the International Searching Authority for PCT/US22/52151.

* cited by examiner

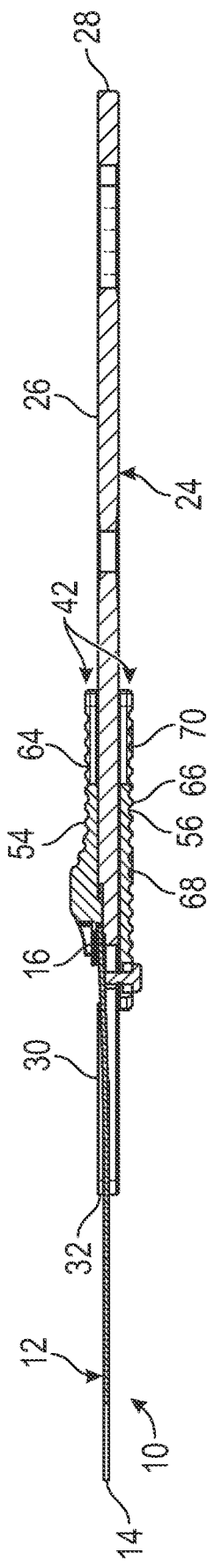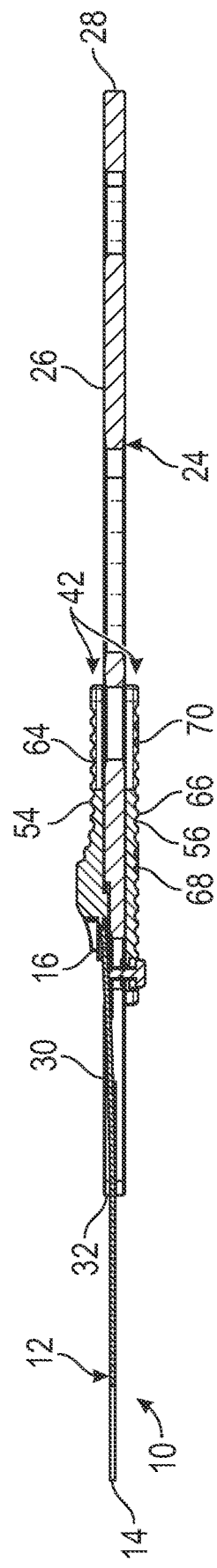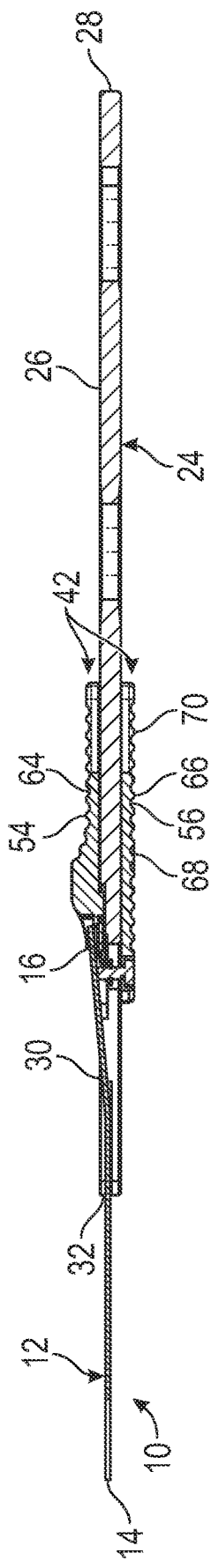

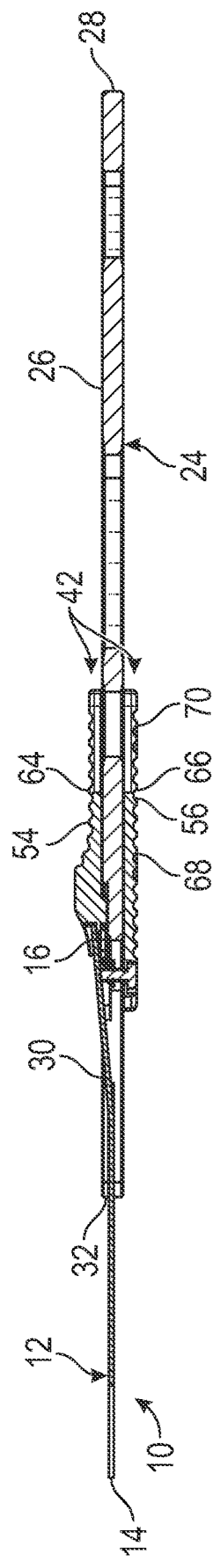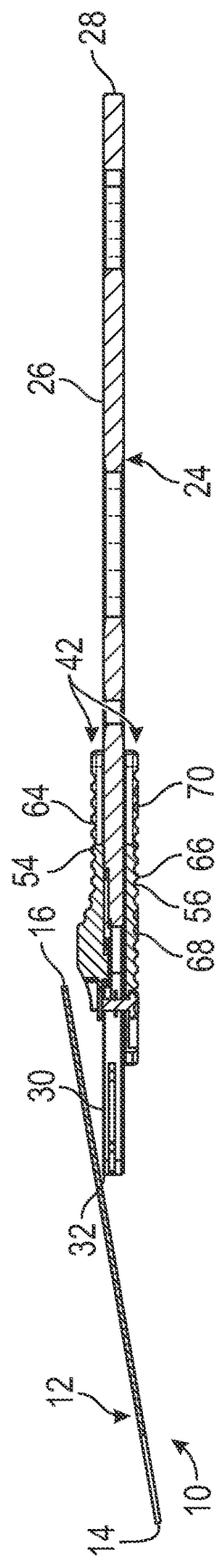

REPLACEABLE BLADE KNIFE

CROSS-REFERENCE TO RELATED APPLICATION

This application claims the benefit of U.S. Provisional Patent Application No. 63/287,107 filed on Dec. 8, 2021, entitled "REPLACEABLE BLADE KNIFE," which is hereby incorporated by reference in its entirety for all that is taught and disclosed therein.

FIELD OF THE INVENTION

The present invention relates to knives, and more particularly to a replaceable blade knife that restrains the blade in use while also reliably ejecting the blade in a safe manner.

BACKGROUND AND SUMMARY OF THE INVENTION

Hunting knives are a common tool for the outdoorsman. They are considered one of the most important items to be carried during any wilderness activity. To ensure ease of carry, the hunting knife should be as light as possible and no larger than is necessary to perform an intended task. For example, a hunting knife used for field dressing a deer, wild pig, or other animal to harvest meat must be sufficiently large while remaining light. The hunting knife must also remain sharp throughout the field dressing activity until harvesting is complete. This is where the size of knife and other factors, such as type of knife steel, contribute to the user's knife selection while pre-planning for these field activities.

A common problem occurs when, for a variety of reasons, the selected knife does not stay sharp even after thoughtful planning has occurred. Over the past several years, a solution to this problem has evolved where a knife handle that allows for a replaceable sharp blade has gained universal acceptance and popularity. Some common makers of these knives with replaceable blades are: Havalon Knives of Cincinnati, OH, Gerber Gear of Portland, OR, and Kershaw Knives of Tualatin, OR Many of these relatively new knife products have been designed poorly with respect to overall size and weight, but have succeeded with high praise for their ability to provide a very inexpensive replacement blade in the field to assure a sharp edge regardless of extended heavy cutting activities. The user can replace a dull blade with a new sharp blade as needed until field activities are completed.

While many knife manufacturing companies have acknowledged this trend for products with replaceable blades, Havalon Knives has emerged as the clear leader in this product category. In fact, the word Havalon has become synonymous among users and retailers for this product almost universally. Another contributing element to this universally acknowledged term (Havalon), is that other knife makers have found it more convenient and economical to design and produce products using blades provided by Havalon Knives. These blades can be purchased from Havalon Knives in bulk volume very inexpensively, work very well, and are a proven product that the end user wants and recognizes.

However, some problems with replaceable blade knives have been identified by end users during normal use of these knives. The most concerning is when the replaceable blade becomes unrestrained and slips out of the handle. This happens when the user is manipulating the knife with enough force to bend the rear of the blade high enough to achieve the proper elevation for removal of the blade. When this condition exists, a simple push of the blade or pull of the handle will cause the blade to disengage from the handle, often putting the user in danger of encountering a sharp edge and exposing them to cuts or potentially more serious injury. A second problem occurs when the user has decided to replace a blade under field or other use conditions where their hands might be slippery because they are bloody or greasy. When this condition exists, it is difficult to lift the rear of the blade and push the lifted blade forward far enough to release the blade from the handle. This activity often results in the hand slipping from the grip of the blade and exposing the hand or fingers to the sharp edge of the blade and again exposing the user to potential injury. While other hazards exist, they are more or less similar to virtually all other types of knives.

Replaceable blade knives are also used in the medical field, particularly in surgeries. Similar problems exist where medical personnel are exposed to undesirable risks of being injured because of inadvertent blade detachment or challenges with releasing the blade from the handle. There is also an additional risk of medical personnel being exposed to pathogens in the event they are cut by a used blade.

Therefore, a need exists for a new and improved replaceable blade knife that restrains the blade in use while also reliably ejecting the blade in a safe manner. In this regard, the various embodiments of the present invention substantially fulfill at least some of these needs. In this respect, the replaceable blade knife according to the present invention substantially departs from the conventional concepts and designs of the prior art, and in doing so provides an apparatus primarily developed for the purpose of restraining the blade in use while also reliably ejecting the blade in a safe manner.

The present invention provides an improved replaceable blade knife, and overcomes the above-mentioned disadvantages and drawbacks of the prior art. As such, the general purpose of the present invention, which will be described subsequently in greater detail, is to provide an improved replaceable blade knife that has all the advantages of the prior art mentioned above.

To attain this, the preferred embodiment of the present invention essentially comprises an elongated body having opposed ends, the elongated body having a handle portion extending to a handle end of the elongated body, and a blade attachment facility at an opposed forward end of the elongated body, the blade attachment facility having a blade support surface configured to abut a major face portion of the planar blade proximate the elongated aperture, an elongated boss sized to closely receive the elongated aperture of the planar blade, the elongated boss defining an undercut configured to receive a blade portion at the constriction to prevent separation of the planar blade from the blade support surface when the planar blade is in an installed condition with the elongated boss received in the elongated aperture, and a movable ejector element connected to the elongated body and operable to engage a rear end of the planar blade to eject the planar blade from the holder. There are, of course, additional features of the invention that will be described hereinafter and which will form the subject matter of the claims attached.

There has thus been outlined, rather broadly, the more important features of the invention in order that the detailed description thereof that follows may be better understood and in order that the present contribution to the art may be better appreciated.

BRIEF DESCRIPTION OF THE DRAWINGS

FIG. 5A is a sectional view of the of the replaceable blade knife of FIG. 1 with the movable ejector element in the neutral position.

FIG. 5B is a sectional view of the of the replaceable blade knife of FIG. 1 with the movable ejector element in the retracted position.

FIG. 5C is a sectional view of the of the replaceable blade knife of FIG. 1 with the movable ejector element in the retracted position with the flexure element pressed to lift the blade.

FIG. 5D is a sectional view of the of the replaceable blade knife of FIG. 1 with the movable ejector element in the neutral position with the flexure element held and the blade resting on the ledge of the movable ejector element.

FIG. 5E is a sectional view of the of the replaceable blade knife of FIG. 1 with the movable ejector element in the extraction position with the blade having been ejected.

The same reference numerals refer to the same parts throughout the various figures.

DESCRIPTION OF THE CURRENT EMBODIMENT

Figure 1:
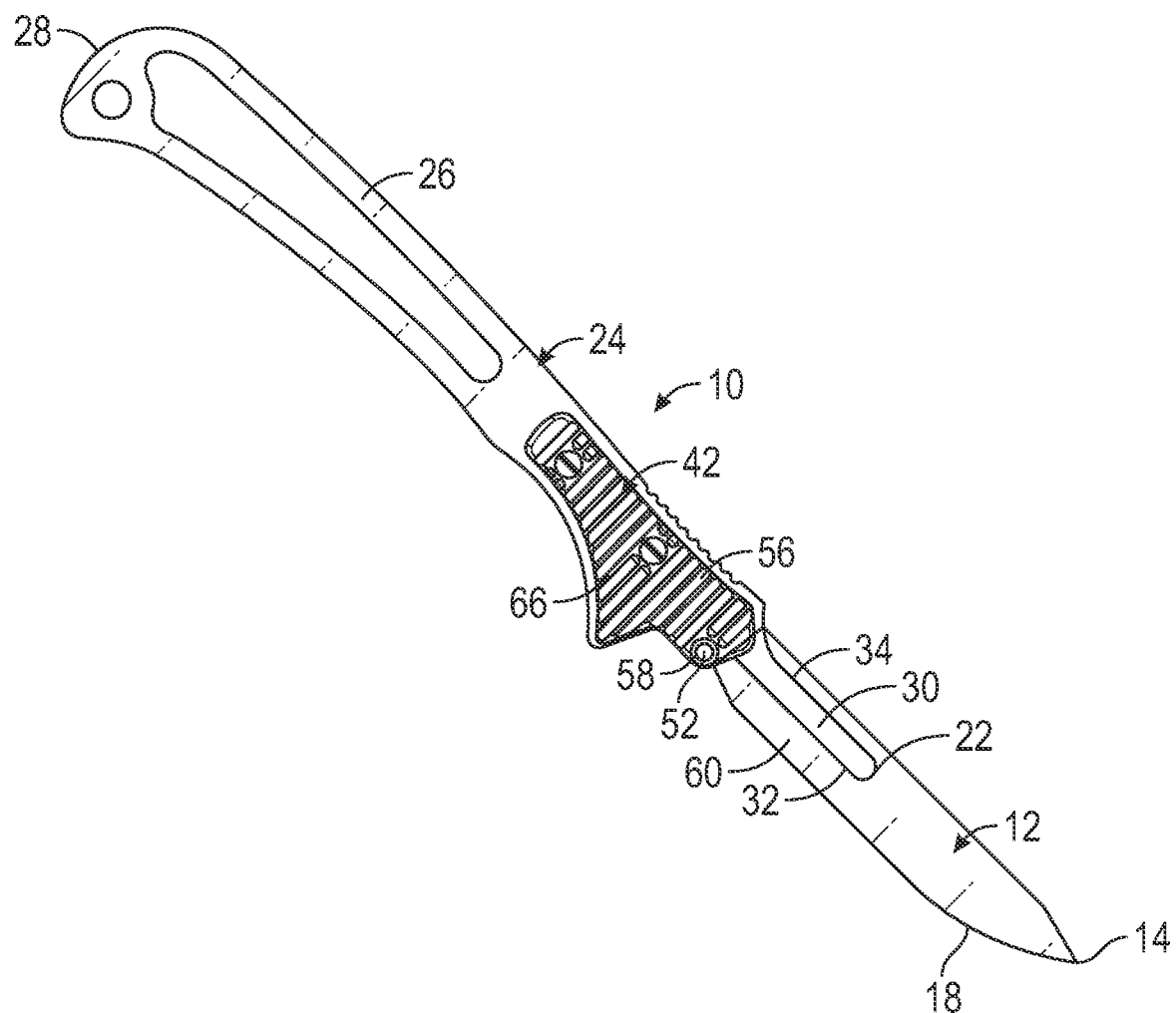
FIG. 1 is an isometric view of the current embodiment of a replaceable blade knife constructed in accordance with the principles of the present invention with the movable ejector element in the neutral position.

An embodiment of the replaceable blade knife of the present invention is shown and generally designated by the reference numeral 10.

Figure 2A:
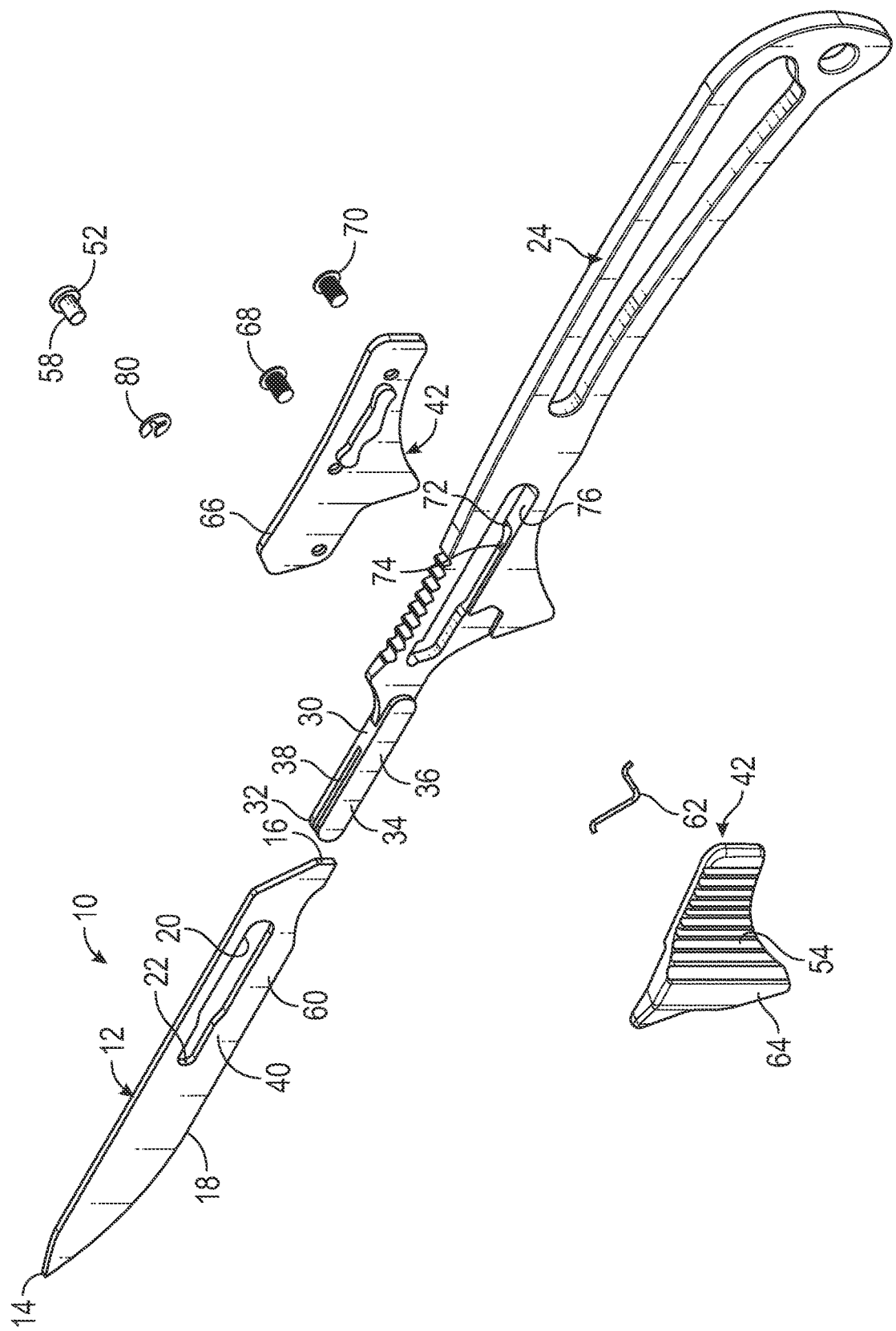
FIG. 2A is an exploded view of the replaceable blade knife of FIG. 1.
Figure 2B:
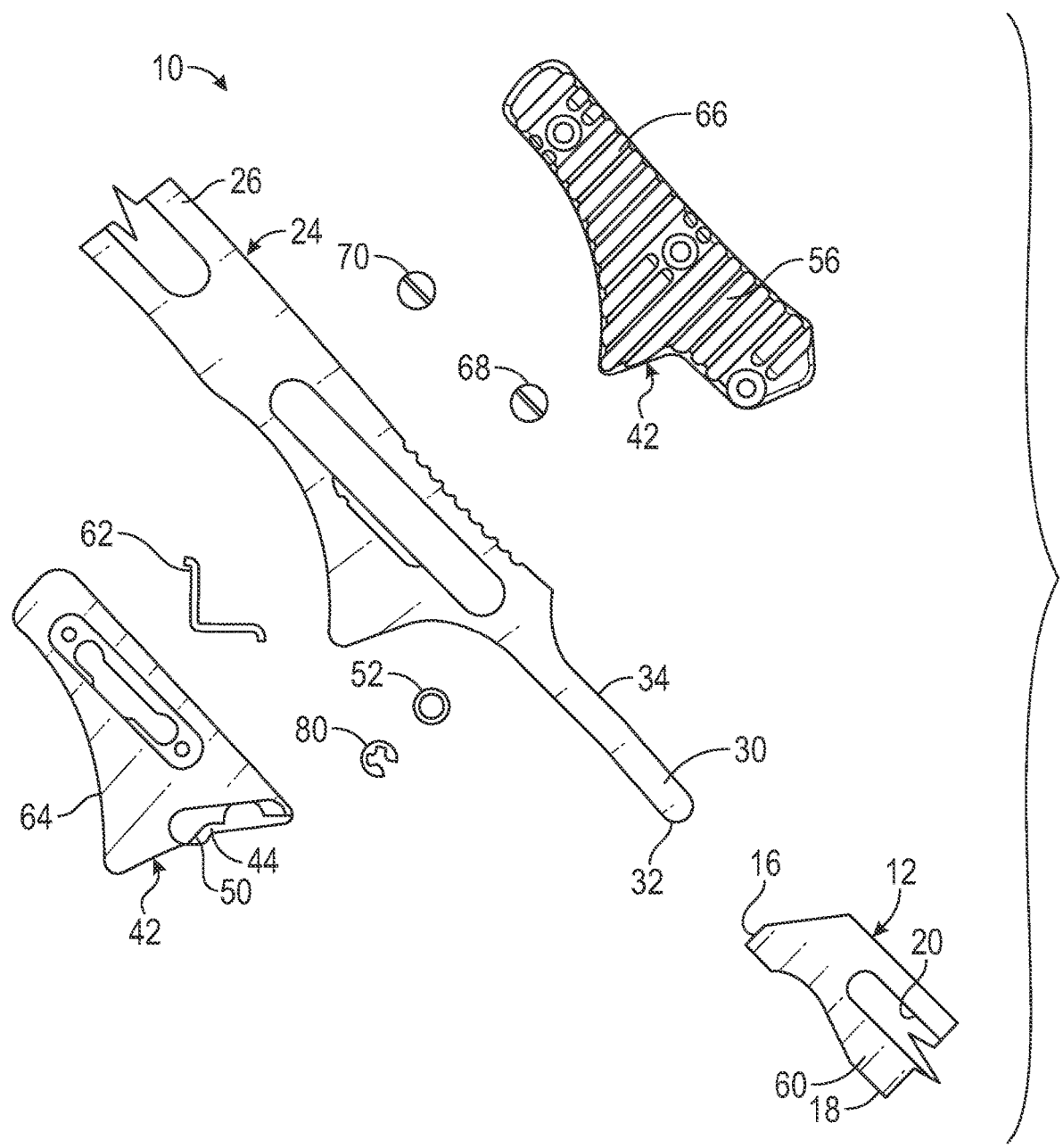
FIG. 2B is an enlarged exploded partial view of the replaceable blade knife of FIG. 1.

FIGS. 1-2B illustrate the improved replaceable blade knife 10 of the present invention. More particularly, the replaceable blade knife is a holder for a planar blade 12 having a forward end 14 and an opposed rear end 16, a sharp edge 18, and defining an elongated aperture 20 having a constriction at one end 22. The holder is an elongated body 24 having opposed ends. The elongated body has a handle portion 26 extending to a handle end 28 of the elongated body, and a blade attachment facility 30 at an opposed forward end 32 of the elongated body. The blade attachment facility has a blade support surface 34 configured to abut a major face portion 60 of the planar blade proximate the elongated aperture. An elongated boss 36 is sized to closely receive the elongated aperture of the planar blade. The elongated boss defines an undercut 38 configured to receive a blade portion 40 at the constriction to prevent separation of the planar blade from the blade support surface when the planar blade is in an installed condition with the elongated boss received in the elongated aperture. A movable ejector element 42 formed by a sliding guard 64 and a sliding rear plate 66 is connected to the elongated body by flat head screws 68, 70. The moveable ejector element is operable to engage the rear end of the planar blade to eject the planar blade from the holder.

Figure 3A:
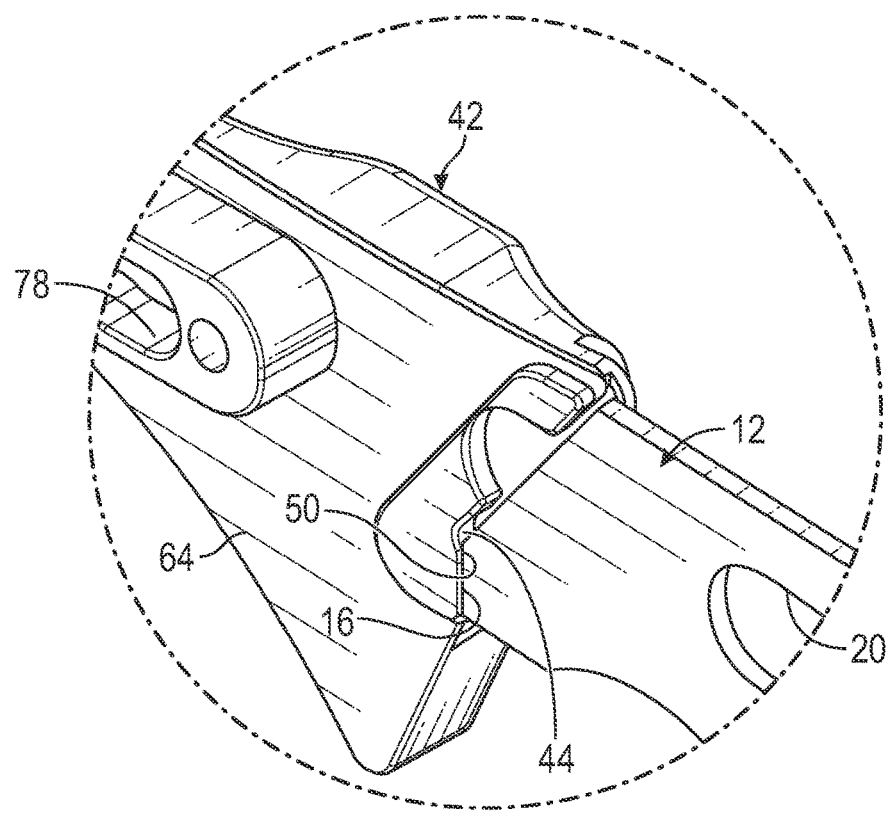
FIG. 3A is an enlarged isometric partial view of the movable ejector element and blade of FIG. 1 with the movable ejector element in the neutral position.
Figure 3B:
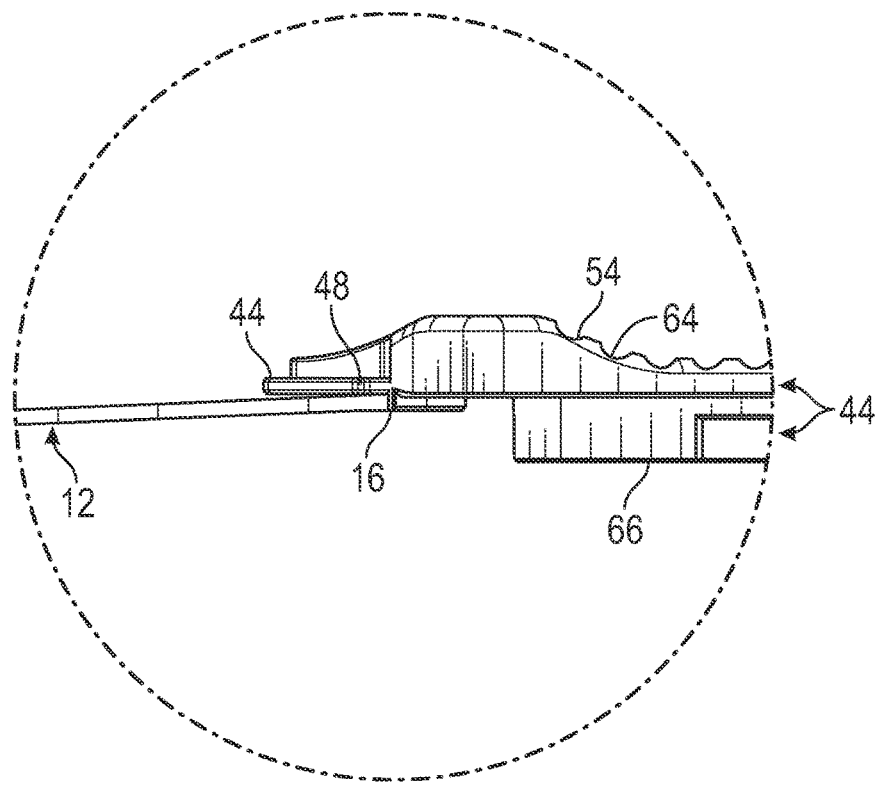
FIG. 3B is an enlarged bottom partial view of the movable ejector element and blade of FIG. 1 with the movable ejector element in the neutral position.

FIGS. 3A & B illustrate the improved movable ejector element 42 and planar blade 12 of the present invention. More particularly, the movable ejector element reciprocates along the length of the elongated body 24 forming the holder. The movable ejector element has a ledge 44 at a different level from the blade support surface 34 and configured to retain the rear end 16 of the planar blade 12 above the blade support surface. The distance between the different level and the blade support surface is adequate to elevate a portion of the planar blade at the rear end of the elongated aperture 20 above a rear end 46 of the elongated boss 36.

Figure 4A:
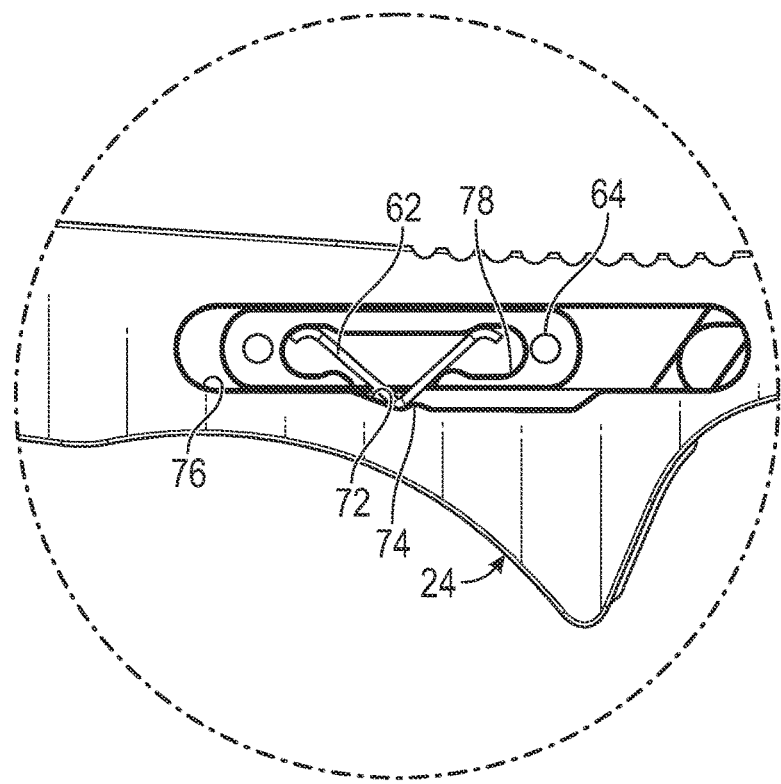
FIG. 4A is an enlarged side partial view of the replaceable blade knife of FIG. 1 with the movable ejector element in the neutral position.
Figure 4B:
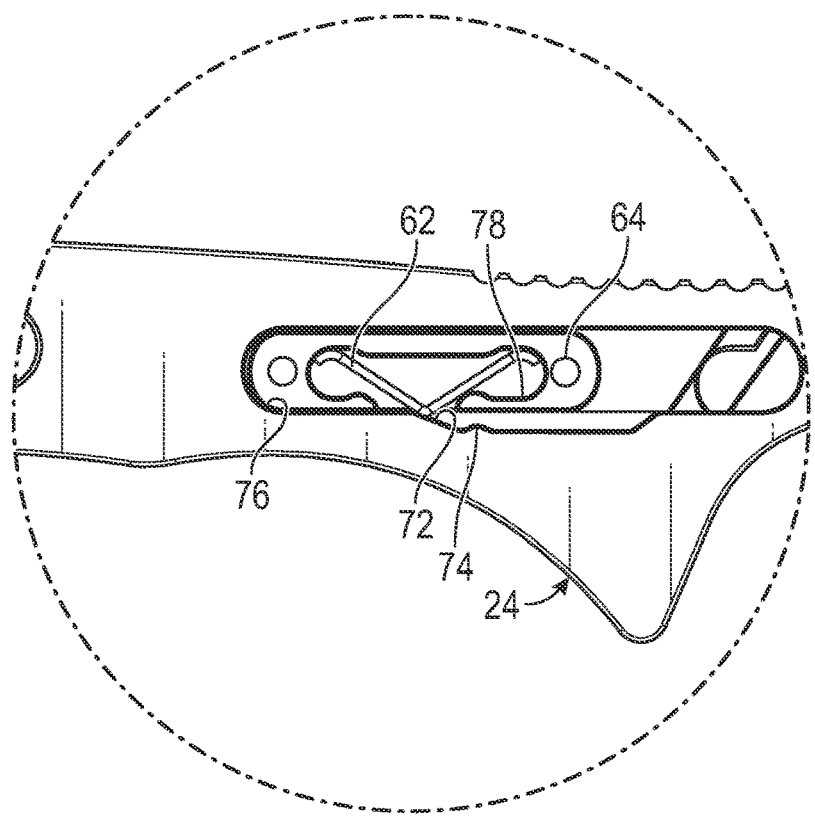
FIG. 4B is an enlarged side partial view of the replaceable blade knife of FIG. 1 with the movable ejector element in the retracted position.
Figure 4C:
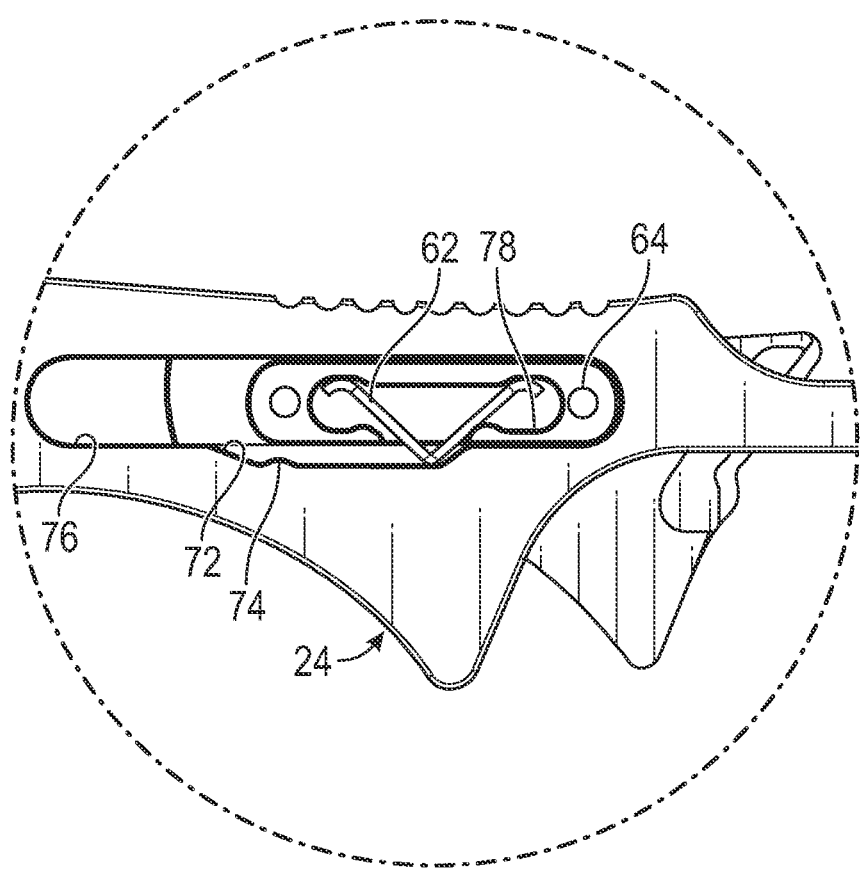
FIG. 4C is an enlarged side partial view of the replaceable blade knife of FIG. 1 with the movable ejector element in the extraction position.

The movable ejector element 42 is movable between a first operational position shown in FIG. 4A in which the planar blade 12 is unflexed and abuts the blade support surface 34, a second position shown in FIG. 4B in which flexure of the rear end 16 of the planar blade away from the blade support surface is enabled, and a third position shown in FIG. 4C in which the movable ejector element is sufficiently forward of the first position to eject the planar blade from the holder.

The movable ejector element 42 includes a blade restraint 48 configured to prevent lateral deviation of the rear end 16 of the planar blade 12 when in the first operational position. In the current embodiment, the movable ejector element is biased toward the first operational position. This biasing is accomplished by a sloped surface 72 and detent 74 defined within a handle aperture 76 defined by the elongated body that interact with a wire form spring 62 protruding from a pocket 78 defined by the sliding guard 64. The movable ejector element has a forward-facing shoulder surface 50 configured to engage the rear end of the planar blade to enable ejection of the planar blade when the rear end of the planar blade is deviated sufficiently above the blade support surface 34. The ledge 44 is adjacent to the forward-facing shoulder surface. The movable ejector element is constrained by the planar blade against movement from the first operational position to the third position when the planar blade is against the blade support surface. The movable ejector element includes an external actuator 52 operably engaged by a user's finger. The external actuator is secured to the elongated body by a retaining ring 80. The movable ejector element has opposed grip surfaces 54, 56 on opposed sides of the holder. The movable ejector element is operable to slide in a direction parallel to the length of the holder. The movable ejector element is at an intermediate position along the length of the holder between the handle portion 26 and the blade attachment facility 30.

A flexure element 58, which extends from the button serving as the external actuator 52 in the current embodiment, is operable to flex the rear end 16 of the planar blade 12 away from the blade support surface 34. The movable ejector element 42 is movable between a first operational position in which the planar blade 12 is unflexed and abuts the blade support surface, a second position to the rear of the first position in which flexure of the rear end of the planar blade away from the blade support surface is enabled, and wherein the flexure element is prevented by contact of the movable ejector element and the planar blade from flexing the planar blade when the movable ejector element is in the first position. The flexure element is connected to the movable ejector element. The flexure element is operated to move laterally with respect to the blade support surface.

The elongated boss 36 is a forward feature at the opposed forward end 32 of the elongated body 24 forming the holder. The elongated boss is partially grooved by the undercut 38 to provide a slightly snug holding feature for the planar blade 12. The slightly snug condition is achieved when the constriction at one end 22 of the elongated aperture 20 of the planar blade slides into the undercut on the elongated boss. To allow disengagement, the planar blade must be flexible enough to bend over the remainder of the elongated boss until full insertion of the constriction is achieved. At this point, the remainder of the elongated aperture is clear of the elongated boss, enabling the opposed rear end 16 of the planar blade to snap down and around the remainder of the elongated boss.

The planar blade 12 is now installed onto the elongated body 24 forming the holder. To remove the planar blade from the elongated body, the user lifts the opposed rear end 16 of the planar blade until the opposed rear end of the planar blade is clear of the elongated boss 36. The user then applies forward pressure to the planar blade so the constriction at one end 22 of the elongated aperture 20 of the planar blade slides out of the grooves on the elongated boss until the elongated aperture is free of the elongated boss. The user can then attach a replacement planar blade to the elongated boss in the manner described previously.

Figure 6A:
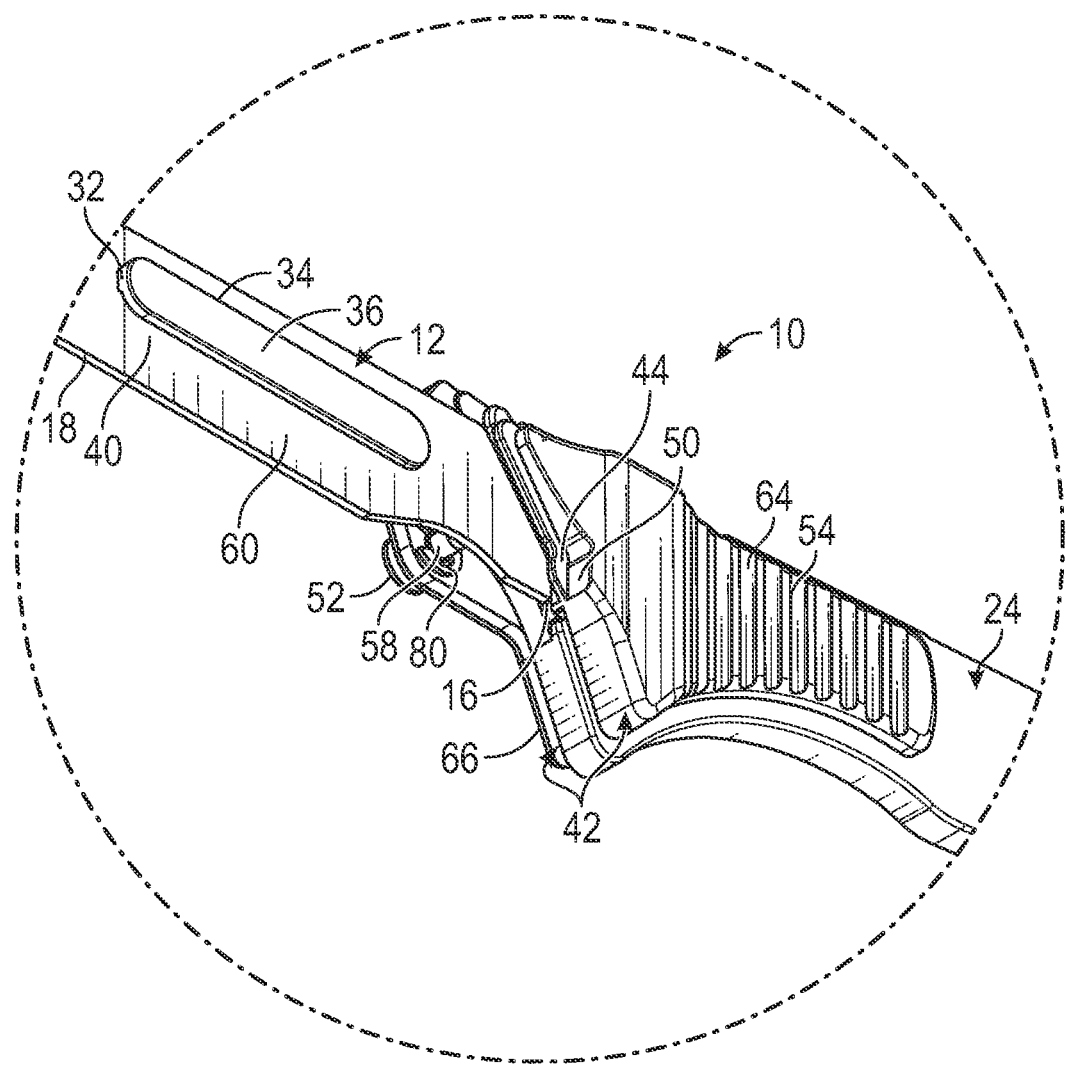
FIG. 6A is an enlarged isometric view of the of the replaceable blade knife of FIG. 1 with the movable ejector element in the neutral position.
Figure 6B:
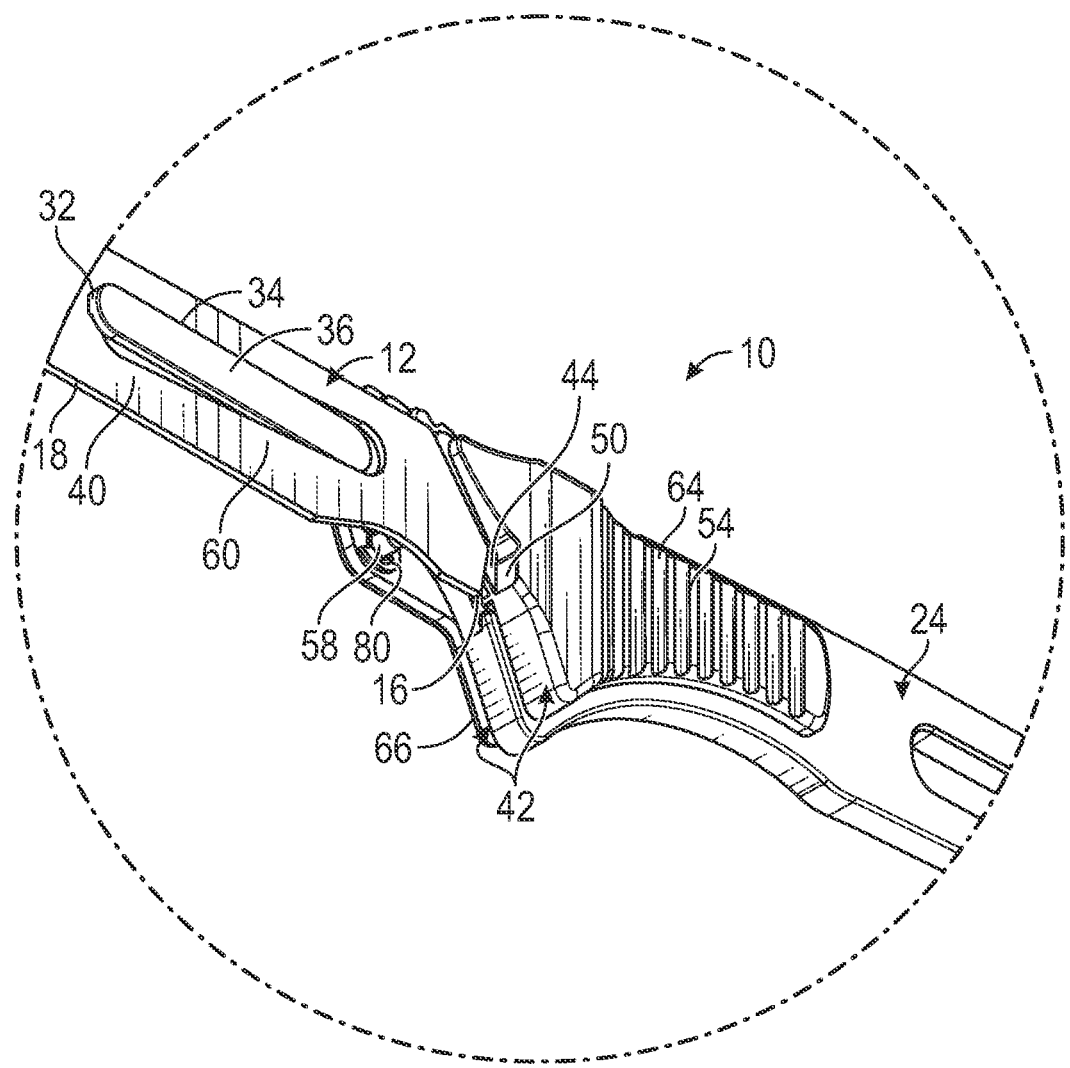
FIG. 6B is an enlarged isometric view of the of the replaceable blade knife of FIG. 1 with the movable ejector element in the retracted position.
Figure 6C:
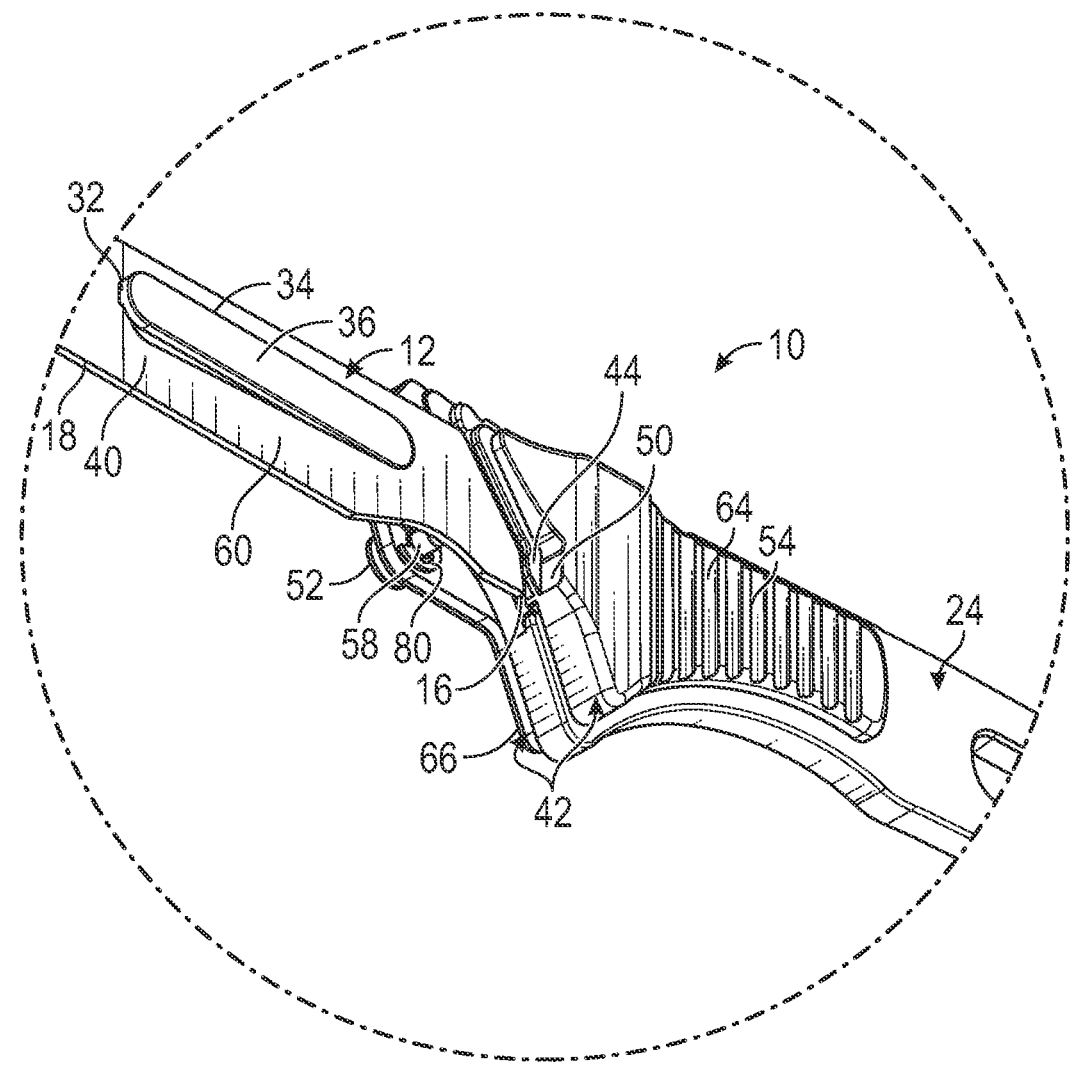
FIG. 6C is an enlarged isometric view of the of the replaceable blade knife of FIG. 1 with the movable ejector element in the retracted position with the flexure element pressed to lift the blade.
Figure 6D:
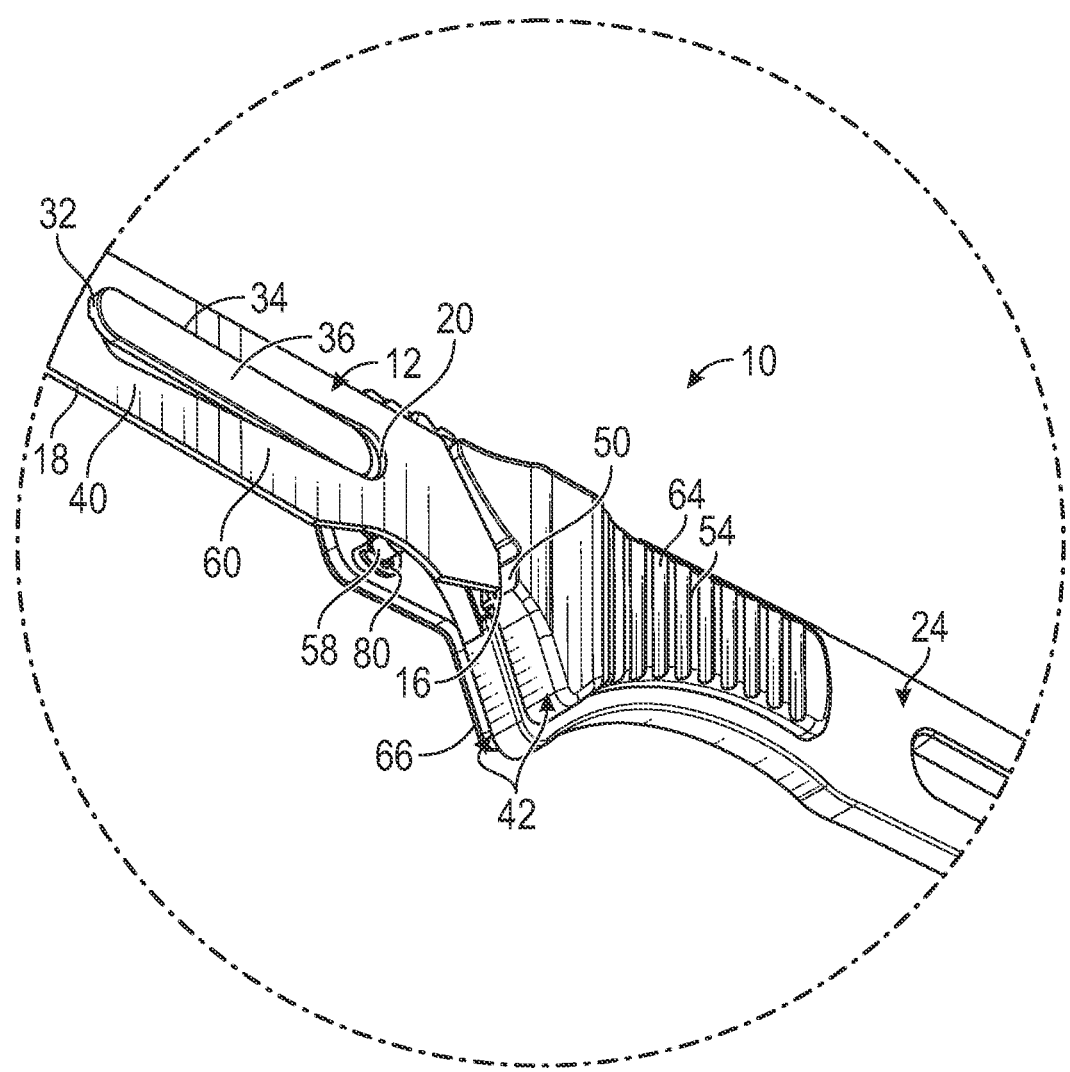
FIG. 6D is an enlarged isometric view of the of the replaceable blade knife of FIG. 1 with the movable ejector element in the neutral position with the flexure element held and the blade resting on the ledge of the movable ejector element.
Figure 6E:
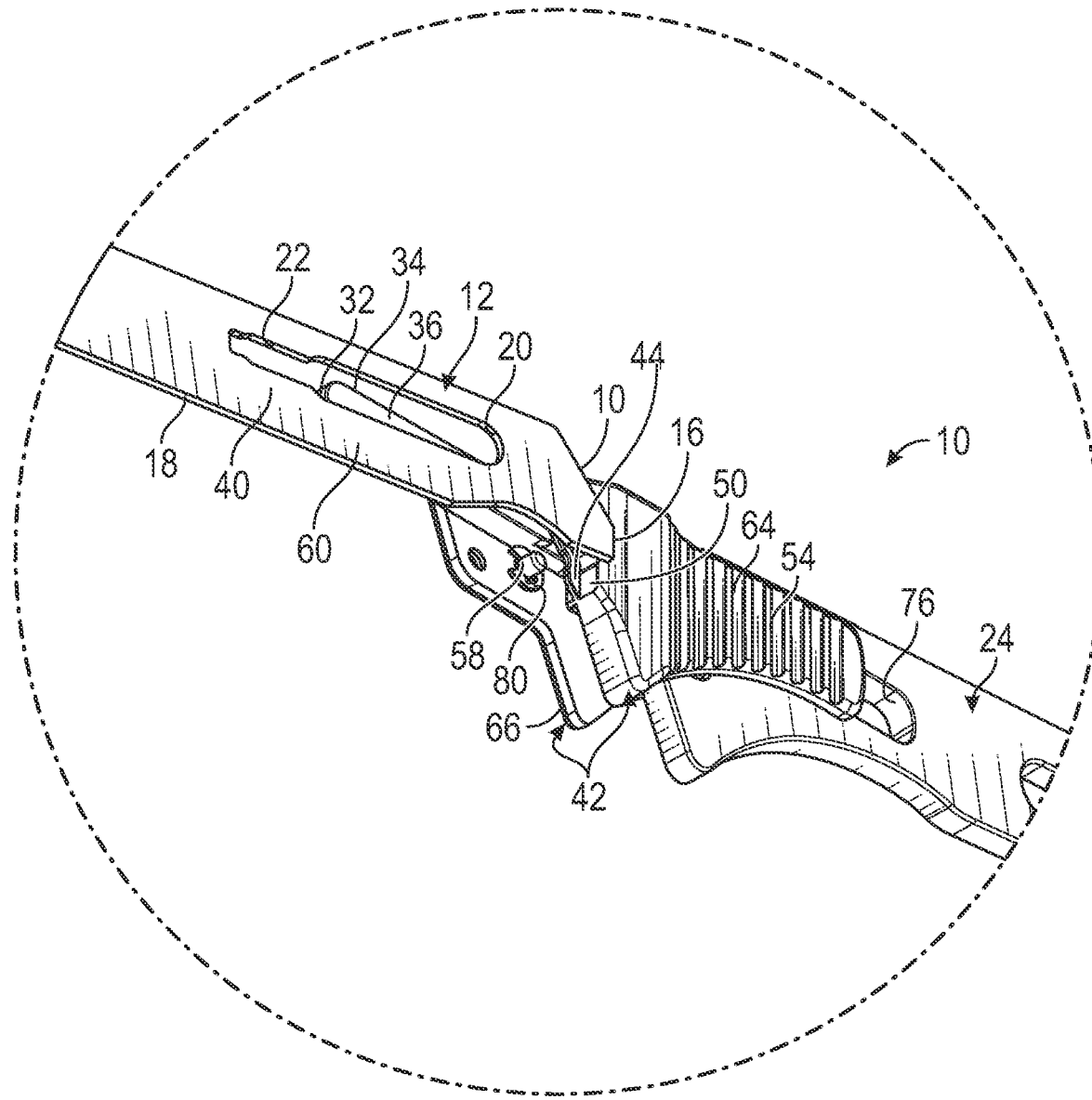
FIG. 6E is an enlarged isometric view of the of the replaceable blade knife of FIG. 1 with the movable ejector element in the extraction position with the blade having been ejected.
Figure 7:
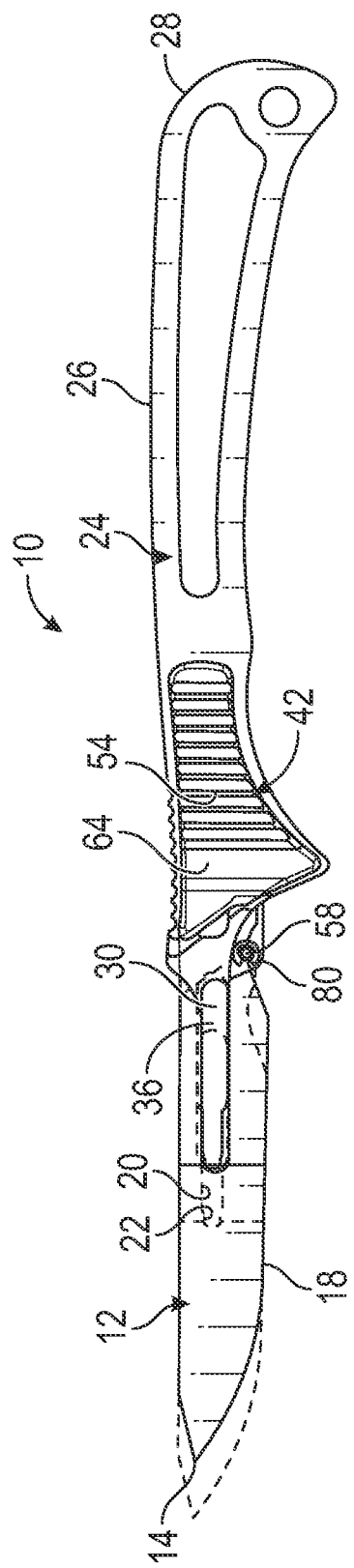
FIG. 7 is a side view of the replaceable blade knife of FIG. 1 with the movable ejector element in the neutral position and dashed lines showing the blade in the ejection position.

FIGS. 5A-6E illustrate the movable ejector element 42 in five staged positions arranged along the length of the elongated body 24 forming the holder. FIG. 7 illustrates the planar blade 12 in the installed condition on the elongated body in solid lines and in the ejected position in dashed lines. In FIGS. 5A & 6A, the movable ejector element is shown in the neutral position with the opposed rear end 16 of the planar blade 12 releasably secured by the blade restraint 48 and ready for use. In FIGS. 5B & 6B, the movable ejector element is shown in the retracted position in preparation for ejecting the planar blade. In FIGS. 5C & 6C, the movable ejector element is shown in the retracted position with the opposed rear end of the planar blade lifted for ejection by the flexure element 58. In FIGS. 5D & 6D, the movable ejector element is shown having returned to the neutral position with the opposed rear end of the planar blade resting on top of the ledge 44. In FIGS. 5E & 6E, the movable ejector element is shown in the forwardmost position ejecting the planar blade with the constriction at one end 22 of the elongated aperture 20 of the planar blade having slid out of the grooves on the elongated boss 36 in the process of being ejected.

In the neutral position, the blade restraint 48 of the movable ejector element 42 covers the opposed rear end 16 of the planar blade 12. This prevents the opposed rear end of the planar blade from lifting above the elongated boss 36, thereby preventing the blade from becoming dislodged from the elongated body 24 forming the holder. In the neutral position, the movable ejector element is biased forward of the retracted position by a wire form spring 62. The movable ejector element is obstructed from moving forward of the neutral position by the opposed rear end of the installed planar blade. Because the movable ejector element is spring-biased forward against the installed planar blade, the replaceable blade knife 10 will perform much more reliably, and the user will be permitted to exert much more force in a variety of manipulations and cutting activities without dislodging the planar blade, than is possible with conventional replaceable blade knives.

The user must exert sufficient force to overcome the wire form spring 62 to move the movable ejector element 42 rearward to the retracted position to initiate ejection of the planar blade 12. The forward spring-bias exerted by the wire form spring makes it easy for the user to slide the movable ejector element 42 forward under the lifted opposed rear end 16 of the planar blade until the opposed rear end of the planar blade rests on the top of the ledge 44.

At this point, the movable ejector element 42 has returned to the neutral position. However, further forward movement of the movable ejector element is now possible because the opposed rear end 16 of the planar blade 12 no longer blocks the movable ejector element. As a result, the user can continue to push the movable ejector element forward, which pushes the planar blade forward and disengages the constriction at one end 22 of the elongated aperture 20 from the grooves on the elongated boss 36. Once the movable ejector element reaches the forwardmost position, the elongated aperture is completely disengaged from the elongated boss, and the planar blade is fully ejected from the elongated body 24 forming the holder.

It should be appreciated that the movable ejector element 42 and the flexure element 58 enable the user to lift the opposed rear end 16 of the planar blade 12 and subsequently push the planar blade 12 off the elongated boss 36 to eject the planar blade without having to directly contact the planar blade with their fingers. As a result, the blade ejection procedure is much safer for the user and easier to perform with fingers made slippery by blood or grease compared to conventional replaceable blade knives.

While a current embodiment of a replaceable blade knife has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A holder for a planar blade having a forward end and an opposed rear end, a sharp edge, and defining an elongated aperture having a constriction at one end, the holder comprising:
an elongated body having opposed ends;
the elongated body having a handle portion extending to a handle end of the elongated body, and a blade attachment facility at an opposed forward end of the elongated body;
the blade attachment facility having a blade support surface configured to abut a major face portion of the planar blade proximate the elongated aperture;
an elongated boss sized to closely receive the elongated aperture of the planar blade;
the elongated boss defining an undercut configured to receive a blade portion at the constriction to prevent separation of the planar blade from the blade support surface when the planar blade is in an installed condition with the elongated boss received in the elongated aperture;
a movable ejector element connected to the elongated body and operable to engage the rear end of the planar blade to eject the planar blade from the holder; and
a flexure element movable with respect to the ejector and operable to flex the rear end of the planar blade away from the blade support surface.

2. The holder of claim 1 wherein the movable ejector element reciprocates along the length of the holder.

3. A holder for a planar blade having a forward end and an opposed rear end, a sharp edge, and defining an elongated aperture having a constriction at one end, the holder comprising:
an elongated body having opposed ends;
the elongated body having a handle portion extending to a handle end of the elongated body, and a blade attachment facility at an opposed forward end of the elongated body;
the blade attachment facility having a blade support surface configured to abut a major face portion of the planar blade proximate the elongated aperture;
an elongated boss sized to closely receive the elongated aperture of the planar blade;
the elongated boss defining an undercut configured to receive a blade portion at the constriction to prevent separation of the planar blade from the blade support surface when the planar blade is in an installed condition with the elongated boss received in the elongated aperture;
a movable ejector element connected to the elongated body and operable engage the rear end of the planar blade to eject the planar blade from the holder; and
wherein the movable ejector element has a ledge at a different level from the blade support surface and configured to retain the rear end of the planar blade above the blade support surface.

4. The holder of claim 3 wherein the distance between the different level and the blade support surface is operable to elevate a portion of the planar blade at the rear end of the elongated aperture above a rear end of the elongated boss.

5. A holder for a planar blade having a forward end and an opposed rear end, a sharp edge, and defining an elongated aperture having a constriction at one end, the holder comprising:
an elongated body having opposed ends;
the elongated body having a handle portion extending to a handle end of the elongated body, and a blade attachment facility at an opposed forward end of the elongated body;
the blade attachment facility having a blade support surface configured to abut a major face portion of the planar blade proximate the elongated aperture;
an elongated boss sized to closely receive the elongated aperture of the planar blade;
the elongated boss defining an undercut configured to receive a blade portion at the constriction to prevent separation of the planar blade from the blade support surface when the planar blade is in an installed condition with the elongated boss received in the elongated aperture;
a movable ejector element connected to the elongated body and operable engage the rear end of the planar blade to eject the planar blade from the holder; and
wherein the movable ejector element has a ledge at a different level from the blade support surface and configured to retain the rear end of the planar blade above the blade support surface.

6. The holder of claim 5 wherein the movable ejector element includes a blade restraint configured to prevent lateral deviation of the rear end of the planar blade when in the first operational position.

7. The holder of claim 5 wherein the movable ejector element is biased toward the first operational position.

8. A holder for a planar blade having a forward end and an opposed rear end, a sharp edge, and defining an elongated aperture having a constriction at one end, the holder comprising:
an elongated body having opposed ends;
the elongated body having a handle portion extending to a handle end of the elongated body, and a blade attachment facility at an opposed forward end of the elongated body;
the blade attachment facility having a blade support surface configured to abut a major face portion of the planar blade proximate the elongated aperture;
an elongated boss sized to closely receive the elongated aperture of the planar blade;
the elongated boss defining an undercut configured to receive a blade portion at the constriction to prevent separation of the planar blade from the blade support surface when the planar blade is in an installed condition with the elongated boss received in the elongated aperture;
a movable ejector element connected to the elongated body and operable engage the rear end of the planar blade to eject the planar blade from the holder;
wherein the movable ejector element has a forward-facing shoulder surface configured to engage a rear end of the planar blade to enable ejection of the planar blade when the rear end of the planar blade is deviated above the blade support surface; and
wherein the movable ejector element has a ledge at a different level from the blade support surface and configured to retain the rear end of the planar blade above the blade support surface, and wherein the ledge is adjacent to the forward-facing should surface.

9. The holder of claim 5 wherein the movable ejector element is constrained by the planar blade against movement from the first operational position to the third position when the planar blade is against the blade support surface.

10. The holder of claim 1 wherein the movable ejector element includes an external actuator operably engaged by a user's finger.

11. The holder of claim 1 wherein the movable ejector element has opposed grip surfaces on opposed sides of the holder.

12. The holder of claim 1 wherein the movable ejector element is operable to slide in a direction parallel to the length of the holder.

13. The holder of claim 1 wherein the movable ejector element is at an intermediate position along the length of the holder between the handle and the blade attachment facility.

14. A holder for a planar blade having a forward end and an opposed rear end, a sharp edge, and defining an elongated aperture having a constriction at one end, the holder comprising:
    an elongated body having opposed ends;
    the elongated body having a handle portion extending to a handle end of the elongated body, and a blade attachment facility at an opposed forward end of the elongated body;
    the blade attachment facility having a blade support surface configured to abut a major face portion of the planar blade proximate the elongated aperture;
    an elongated boss sized to closely receive the elongated aperture of the planar blade;
    the elongated boss defining an undercut configured to receive a blade portion at the constriction to prevent separation of the planar blade from the blade support surface when the planar blade is in an installed condition with the elongated boss received in the elongated aperture;
    a movable ejector element connected to the elongated body and operable engage the rear end of the planar blade to eject the planar blade from the holder;
    including a flexure element operable to flex the rear end of the planar blade away from the blade support surface; and
    wherein the movable ejector element is movable between a first operational position in which the planar blade is unflexed and abuts the blade support surface, a second position to the rear of the first position in which flexure of the rear end of the planar blade away from the blade support surface is enabled, and wherein the flexure element is prevented by contact of the movable ejector element and the planar blade from flexing the planar blade when the movable ejector element is in the first position.

15. A holder for a planar blade having a forward end and an opposed rear end, a sharp edge, and defining an elongated aperture having a constriction at one end, the holder comprising:
    an elongated body having opposed ends;
    the elongated body having a handle portion extending to a handle end of the elongated body, and a blade attachment facility at an opposed forward end of the elongated body;
    the blade attachment facility having a blade support surface configured to abut a major face portion of the planar blade proximate the elongated aperture;
    an elongated boss sized to closely receive the elongated aperture of the planar blade;
    the elongated boss defining an undercut configured to receive a blade portion at the constriction to prevent separation of the planar blade from the blade support surface when the planar blade is in an installed condition with the elongated boss received in the elongated aperture;
    a movable ejector element connected to the elongated body and operable engage the rear end of the planar blade to eject the planar blade from the holder;
    including a flexure element operable to flex the rear end of the planar blade away from the blade support surface; and
    wherein the flexure element is connected to the movable ejector element.

16. The holder of claim 15 wherein the flexure element is operated to move laterally with respect to the blade support surface.

17. A holder for a planar blade having a forward end and an opposed rear end, a sharp edge, and defining an elongated aperture having a constriction at one end, the holder comprising:
    an elongated body having opposed ends;
    the elongated body having a handle portion extending to a handle end of the elongated body, and a blade attachment facility at an opposed forward end of the elongated body;
    the blade attachment facility having a blade support surface configured to abut a major face portion of the planar blade proximate the elongated aperture;
    an elongated boss sized to closely receive the elongated aperture of the planar blade;
    the elongated boss defining an undercut configured to receive a blade portion at the constriction to prevent separation of the planar blade from the blade support surface when the planar blade is in an installed condition with the elongated boss received in the elongated aperture;
    a movable ejector element connected to the elongated body and operable to engage the rear end of the planar blade to eject the planar blade from the holder; and
    a flexure element operable to flex the rear end of the planar blade away from the blade support surface.

* * * * *